United States Patent [19]

Simon et al.

[11] Patent Number: 5,769,091
[45] Date of Patent: *Jun. 23, 1998

[54] URETHRAL PLUG HAVING ADHESIVE FOR ENHANCED SEALING CAPABILITIES AND METHOD OF USING SAID PLUG

[75] Inventors: John G. Simon, Boston; Paul D. McLaughlin, Scituate, both of Mass.; Leo C. Felice, Pascoag, R.I.; Sharad Joshi, Watertown, Mass.; Azhar Syed, Brookline, Mass.; Richelle Tartacower, Aktinson, N.H.; Jonathan O'Keefe, Hingham, Mass.

[73] Assignee: UroMed Corporation, Needham, Mass.

[ * ] Notice: The term of this patent shall not extend beyond the expiration date of Pat. No. 5,509,427.

[21] Appl. No.: 599,636

[22] Filed: Feb. 9, 1996

Related U.S. Application Data

[63] Continuation-in-part of Ser. No. 124,264, Sep. 20, 1993, Pat. No. 5,509,427.

[51] Int. Cl.[6] ...................................................... A61F 5/48
[52] U.S. Cl. ................................. 128/885; 128/DIG. 25; 600/29
[58] Field of Search ........................... 128/885, DIG. 25; 604/329, 330, 349–356; 600/29–31

[56] References Cited

U.S. PATENT DOCUMENTS

| | | | |
|---|---|---|---|
| 2,324,520 | 7/1943 | Lamson | 128/283 |
| 2,494,393 | 1/1950 | Lamson | 128/1 |
| 2,638,093 | 5/1953 | Kulick | 128/133 |
| 3,503,400 | 3/1970 | Osthagen et al. | 128/349 |
| 3,646,929 | 3/1972 | Bonnar | 128/1 |
| 3,726,277 | 4/1973 | Hirschman | 128/285 |
| 3,789,828 | 2/1974 | Schulte | 128/1 R |
| 3,797,478 | 3/1974 | Walsh et al. | 128/1 R |
| 3,841,304 | 10/1974 | Jones | 128/1 R |
| 3,857,394 | 12/1974 | Alemany | 128/260 |
| 4,019,499 | 4/1977 | Fitzgerald | 128/1 R |
| 4,258,704 | 3/1981 | Hill | 128/1 |
| 4,261,340 | 4/1981 | Baumel et al. | 128/1 |
| 4,428,365 | 1/1984 | Hakky | 128/1 |
| 4,457,299 | 7/1984 | Cornwell | 128/1 R |
| 4,553,533 | 11/1985 | Leighton | 128/1 |
| 4,563,183 | 1/1986 | Barrodale | 604/329 |
| 4,568,339 | 2/1986 | Steer | 604/329 |

(List continued on next page.)

FOREIGN PATENT DOCUMENTS

| | | | |
|---|---|---|---|
| WO 8810106 | 12/1988 | WIPO | A61F 2/48 |
| WO 8900030 | 1/1989 | WIPO | A61B 19/00 |
| WO 9004431 | 5/1990 | WIPO | A61M 29/00 |
| WO 9219192 | 11/1992 | WIPO | A61F 5/48 |

OTHER PUBLICATIONS

Nielsen et al., "The Urethral Plug: A New Treatment Modality For Genuine Urinary Stress Incontinence in Women", copyright 1990, pp. 1199–1202, Journal of Urology, vol. 144.

*Primary Examiner*—Michael A. Brown
*Attorney, Agent, or Firm*—Lorusso & Loud

[57] ABSTRACT

A novel urethral plug having adhesive thereon, wherein the adhesive seals the plug against the tissues surrounding the meatus and/or urethra, thereby arresting movement of the plug while it functions in the urethra to block the flow of urine. The urethral plug comprises a hollow or solid body which is of a sufficient length and diameter to occlude the urethra. In one embodiment, adhesive is disposed on the meatal plate of the plug so as to secure the plug against the tissues surrounding the urethral meatus. In a second embodiment, adhesive is disposed on the body of the plug so as to seal the plug against the urethral wall. In a third embodiment, the adhesive is disposed on a portion of the meatal plate so as to seal the plug against the tissues surrounding the urethral meatus. The adhesive seals the urethral plug in place until the user wishes to void, at which time, the seal may be broken by exerting a pulling force on the plug.

31 Claims, 4 Drawing Sheets

U.S. PATENT DOCUMENTS

| | | | |
|---|---|---|---|
| 4,682,592 | 7/1987 | Thoregard | 128/303 R |
| 4,822,347 | 4/1989 | MacDougall | 604/329 |
| 4,846,784 | 7/1989 | Haber | 600/29 |
| 4,850,963 | 7/1989 | Sparks et al. | 600/29 |
| 4,938,759 | 7/1990 | Enscore et al. | 604/896.1 |
| 4,946,449 | 8/1990 | Davis, Jr. | 604/256 |
| 4,981,465 | 1/1991 | Ballan et al. | 600/32 |
| 5,012,822 | 5/1991 | Schwarz | 128/885 |
| 5,074,855 | 12/1991 | Rosenbluth et al. | 604/385.1 |
| 5,090,424 | 2/1992 | Simon et al. | 128/885 |
| 5,097,848 | 3/1992 | Schwarz | 128/885 |
| 5,114,380 | 5/1992 | Larsen | 452/176 |
| 5,114,398 | 5/1992 | Trick et al. | 600/29 |
| 5,116,387 | 5/1992 | Berg | 623/66 |
| 5,131,906 | 7/1992 | Chen | 600/29 |
| 5,234,409 | 8/1993 | Goldberg et al. | 604/96 |
| 5,336,208 | 8/1994 | Rosenbluth et al. | 604/329 |
| 5,483,976 | 1/1996 | McLaughlin et al. | 128/885 |
| 5,509,427 | 4/1996 | Simon | 128/885 |

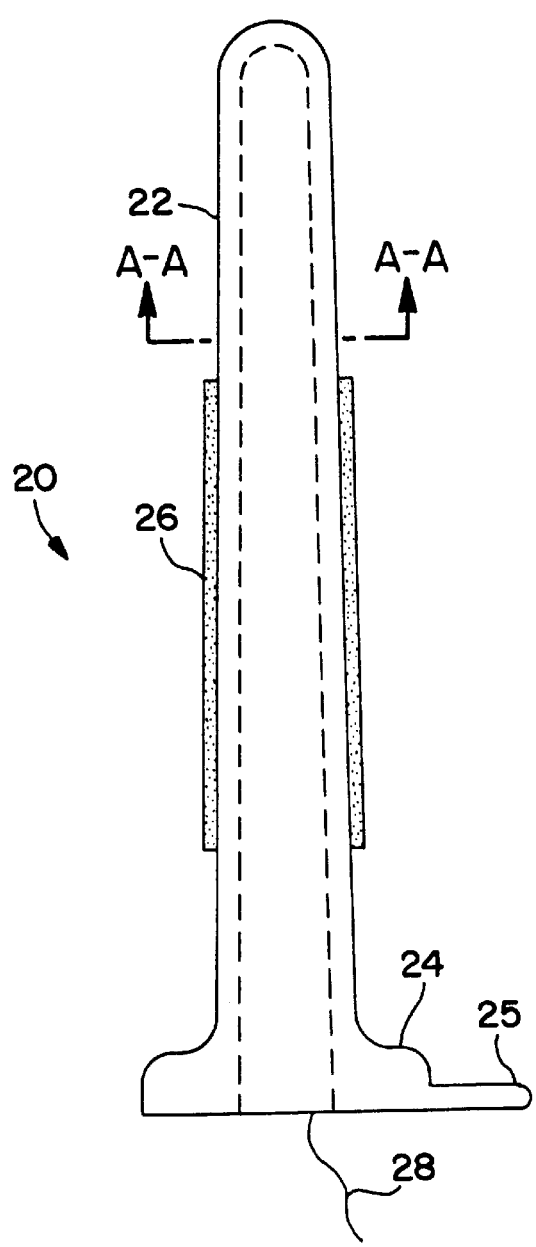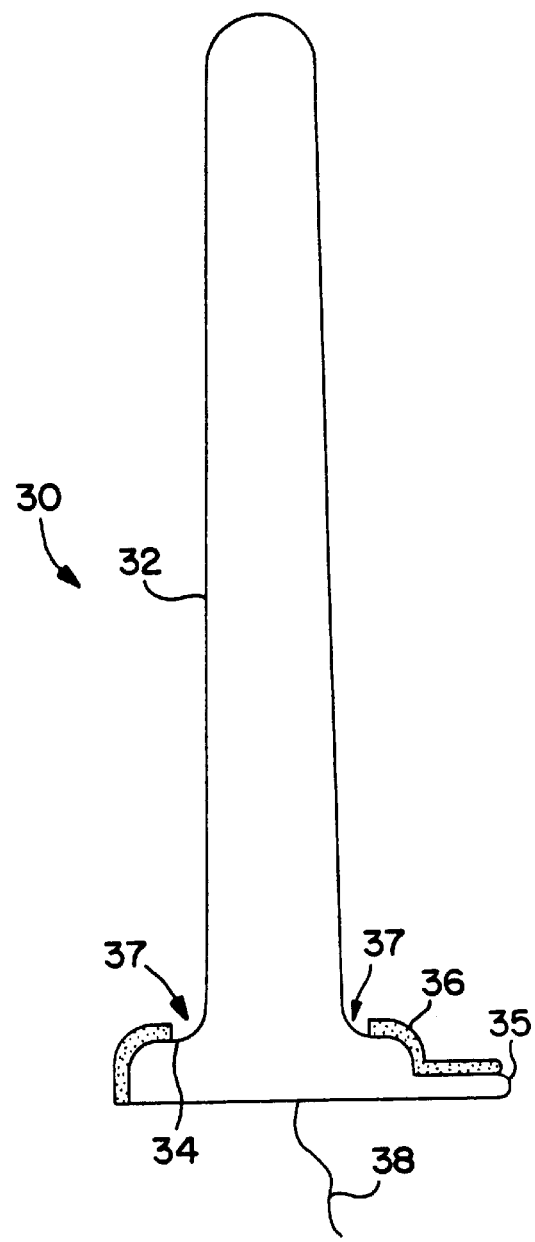
FIG. 2
FIG. 3

URETHRAL PLUG HAVING ADHESIVE FOR ENHANCED SEALING CAPABILITIES AND METHOD OF USING SAID PLUG

CROSS REFERENCE TO A RELATED APPLICATION

This application is a continuation-in-part of U.S. application Ser. No. 08/124,264 filed Sep. 20, 1993 now U.S. Pat. No. 5,509,427, the teachings of which are incorporated herein by reference.

FIELD OF THE INVENTION

This invention relates to the control of urinary incontinence and is directed more particularly to a urethral plug having an adhesive coating thereon, enabling the plug to maintain stability in the urethra.

BACKGROUND OF THE INVENTION

Urinary stress incontinence is the involuntary loss of urine when the pressure within the urethra exceeds the maximum urethral pressure required for maintaining closure or continence. Maximum urethral pressure is exceeded during physical stress, or increased abdominal pressure, from activities such as sneezing, laughing or lifting. While the problem of urinary incontinence occurs in both men and women, it is an affliction especially common in women of child bearing age and older.

There are in existence many methods used to address the problem of incontinence, including surgical corrective techniques, surgically implanted indwelling devices, physician prescribed and inserted indwelling devices, and externally worn devices that collect or absorb urine. Each method has its drawbacks.

Surgically implanted devices may not be appropriate for patients with mild incontinence, or for those with other medical conditions that place them at risk for surgery. Additionally, one must consider the costs of surgery. There are also the problems of encrustation, irritation, infection, toxic reactions to materials, and tissue necrosis with surgically implanted devices. Moreover, surgically implanted devices traditionally have a low long-term success rate.

Indwelling devices that are inserted into the urethra by a physician, without involving surgical implantation, are also known. These devices are inserted through the urethral orifice and allow the user to void either past or through the device. These devices generally are complicated, difficult to manufacture and, therefore, expensive. In practice, such devices have proven difficult to use for the patient as they are uncomfortable and can be cumbersome to manipulate to void. Additionally, these devices, because they are indwelling, may cause some of the numerous complications associated with surgically implanted devices, such as encrustation, irritation and infection.

Also known are devices capable of being inserted by the user into the urethra. Such devices are removed for voiding and then reintroduced into the urethra upon completion of bladder evacuation. An example of such a device is described by Neilsen, Kurt K. et al., in "The Urethral Plug: A New Treatment Modality for Genuine Urinary Stress Incontinence in Women," *J. Urology*, vol. 44, p. 1100 (1990). This device consists of one or two solid spheres located along a soft shaft, and a thin, soft plate located at the end of the shaft. One sphere is located upstream of the maximum urethral closing pressure point, corresponding to the location of the sphincter. In the two sphere embodiment, the second sphere is located with its midpoint at the bladder neck, and is used to assist in reducing urinary flow and pressure transmission to the urethra so that the sphincter can operate. One problem associated with this device is that the patient must have three urethral closure pressure profiles performed, as well as other examinations, before the device is custom made for the user. Additional problems with this device include placement difficulties and lack of sealing capabilities associated therewith, resulting in inadequate retention and expulsion of the device from the urethra. In addition, discomfort may occur with insertion and removal of the device, due to the size profile and rigidity of the spheres, which spheres maintain a constant diameter during insertion and removal.

Another "remove-to-void" device is disclosed in U.S. Pat. No. 5,090,424, which comprises a conformable urethral plug. The body of the plug forms a cavity which is in fluid communication with a second cavity via a check-valve. Thus, fluid may be pumped into the cavity within the urethra to provide a custom fit. This device, like others depending on fluids or gels for expansion, relies heavily on a fluid-tight valve in order to maintain retention. Should valve failure occur, evacuation would immediately follow.

Certain external devices exist that do not require insertion into the urethra, such as absorbent pads, diapers and the like. Such pads are bulky, susceptible to migration, often lack effectiveness in preventing leakage, and provide no effective protection against undesirable odor. Moreover, these devices are expensive to use over time and are often associated with skin problems of the user.

An example of an external device is disclosed in U.S. Pat. Nos. 5,074,855 and 5,336,208. This device employs adhesive to secure a pad to the vestibule of the user, thereby preventing the escape of urine from the urethra. However, there are disadvantages associated with such a device. Due to the structure and function of the device, there is nothing to increase urethral resistance to urine flow. Moreover, as such a pad is designed only to be worn externally, it is subject to migration in the course of one's daily movement and activities, even with the use of adhesive, given the friction associated with undergarments contacting the pad. Migration as such, increases the likelihood of accidents and leakage.

As evidenced by the above discussion, the prior art devices do not address, or inadequately address, problems associated with the stability of urinary incontinence devices. The prior art has not adequately addressed the need for enhancing the retention and sealing capabilities of the urinary devices.

Ideally, the problem of urinary incontinence is addressed with an easily manipulable, remove-to-void device having enhanced retention and sealing capabilities.

SUMMARY OF THE INVENTION

It is, therefore, an object of the invention to provide a urethral plug that successfully manages the problems associated with urinary stress incontinence, and avoids the risk of complications associated with known devices.

Another object of the invention is to improve the degree of retention of a urethral plug in the urethra.

A further object of the invention is to enhance the sealing ability of a urethral plug with the urethral wall.

Another object of the invention is to enhance the sealing ability of a urethral plug at the tissues surrounding the urethral meatus, such that movement of the plug is arrested.

Another object of the invention is to prevent slippage of a urethral plug while disposed in the urethra.

A further object of the invention is to increase the urethral resistance to urine flow through the urethra.

It is yet another object of the invention to provide a urethral plug which can be manipulated easily by the user.

Still another object of the invention is to provide a method of using a urethral plug to control urinary incontinence.

These and other objects of the invention are carried out by a novel urethral plug having adhesive thereon, wherein the adhesive seals the plug against the tissues surrounding the urethral meatus or, alternatively, the urethra. The plug comprises a solid or hollow body which is of sufficient length and diameter to occlude the urethra to control incontinence. The portion of the plug that functions to block the flow of urine is the body, and the portion of the plug that serves to anchor the plug at the urethral meatus is the meatal plate. An appendage is associated with the meatal plate, and removal of the plug for bladder evacuation is easily accomplished by grasping and/or pulling the appendage.

In on e embodiment of the invention, a layer of adhesive lies on the meatal plate so as to secure the plug against the tissues surrounding the urethral meatus. In a second embodiment of the invention, a layer of adhesive lies on the body of the plug so as to seal the plug against the urethral wall. In a third embodiment of the invention, an adhesive layer lies on the outer circumference of the meatal plate so as to seal the plug against the tissues surrounding the urethral meatus.

These and other advantages of the invention will be better appreciated from the following detailed description of the preferred embodiments.

BRIEF DESCRIPTION OF THE DRAWINGS

FIG. 2 shows a urethral plug of the invention having adhesive on a portion o f the body of the plug.

FIG. 3 shows a urethral plug of the invention having adhesive on a portion of the meatal plate.

DETAILED DESCRIPTION OF THE PREFERRED EMBODIMENTS

Figure 1:
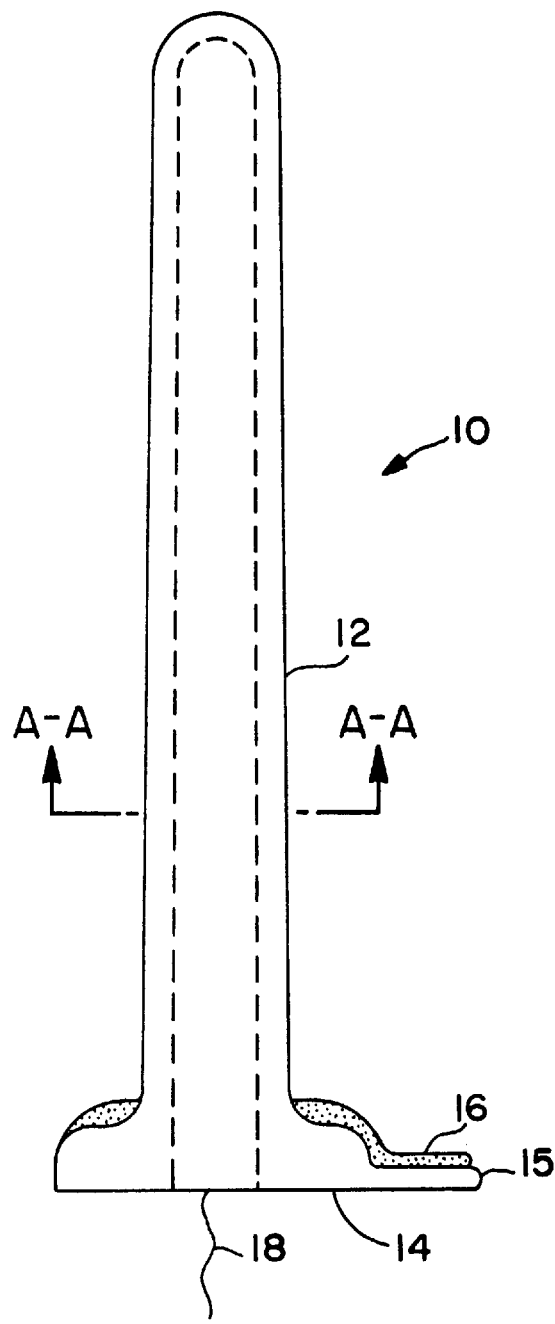
FIG. 1 shows a urethral plug of the invention having adhesive o n the meatal plate.

At the outset, the invention is described in its overall aspects with a more detailed description following. The present invention is a novel urethral plug having adhesive thereon, wherein the adhesive secures the plug against the tissues surrounding the urethral meatus or, alternatively, the urethra. The urethral plug comprises a solid or hollow body which is of sufficient length and diameter to allow occlusion of the urethra. The urethral plug can be made of a soft, flexible biocompatible material such as polyurethane, polyethylene, polypropylene, latex, silicone, foamed urethane, cellulose, polyvinylchloride, DYNAFLEX (a trademark of GLS Corporation, Cary, Ill., for a biocompatible thermoplastic elastomer), KRATON (a trademark of Shell Chemical Company, Houston, Tex., for a biocompatible thermoplastic elastomer), C-FLEX (a trademark of Consolidated Polymer Technologies, Largo, Fla., for a biocompatible thermoplastic elastomer) and the like.

The portion of the urethral plug of the invention that functions to block the flow of urine is the body, and the portion of the plug that serves to anchor the plug at the urethral meatus is the meatal plate. The anchoring of the urethral plug at the meatus prevents the plug from migrating into the bladder. An appendage is affixed to the meatal plate and/or body of the plug, and removal of the plug for bladder evacuation is easily accomplished by grasping and/or pulling the appendage.

In one embodiment of the invention, a layer of adhesive is disposed on the meatal plate so as to secure the plug against the tissues surrounding the urethral meatus. In a second embodiment of the invention, a layer of adhesive is disposed on the body of the plug so as to seal the plug against the urethral wall. In a third embodiment of the invention, an adhesive layer is disposed on the outer circumference of the meatal plate so as to seal the plug against the tissues surrounding the urethral meatus.

The adhesives chosen for use in the present invention may be any adhesive that comfortably bonds to tissue and can subsequently be removed completely by mechanical force. Other objectives may be accomplished by the selection of an appropriate adhesive, for example, it may be useful to have an adhesive that has a low initial tack, but whose tackiness increases in the presence of moisture. Alternatively, strong initial tack may be desired for good long-term adhesion of the plug to the user's tissues.

The adhesive may be selectively applied to the meatal plate and/or body of the plug to provide a number of areas thereon with different adhesive properties. For example, the adhesive may be applied to the meatal plate in a spotty pattern, with each spot consisting of an adhesive with a different property. Or, the layer of adhesive on the meatal plate may be applied in a manner forming concentric rings of adhesive, each ring consisting of an adhesive with a different property. The selected adhesives will be chosen to optimize desired properties.

Preferred adhesives include, but are not limited to, hydrogel adhesives, polyvinylether-based adhesives, hydrocolloid adhesives, acrylic-based adhesives, and natural gum and synthetic rubber adhesives. Other biocompatible adhesive materials known in the art may be used. A removable sheet may be provided over the adhesive to protect the adhesive until the urethral plug is to be used.

Figure 1A:
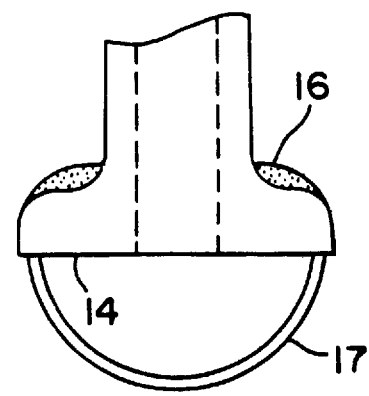
FIG. 1A shows an alternative version of the distal portion of the urethral plugs of the invention without a tab extending from the meatal plate.

Referring first to FIG. 1, shown is a hollow urethral plug 10, having a body 12 sized to allow occlusion of the urethra following insertion of the plug. The length of the body 12 may extend beyond the urethra and into the bladder neck or bladder. A meatal plate 14 is disposed at one end of the body and prevents migration of the urethral plug 10 into the bladder. The meatal plate 14 is a flanged type member having a tab 15, which serves also to prevent migration of the plug 10 into the bladder and aids in removal of the plug 10 when the user wishes to void. Alternatively, the meatal plate 14 of the urethral plug 10 may be provided without the tab, as shown in FIG. 1A.

The meatal plate 14 anchors the urethral plug 10 at the urethral meatus. To carry out this function of anchoring, the meatal plate 14 is of a thickness sufficient to withstand bodily compression during wear, preferably on the order of 0.5 millimeter or greater. Disposed on the meatal plate 14 is a layer of adhesive 16, preferably a hydrogel adhesive. This adhesive layer 16 seals the meatal plate 14 against the tissues surrounding the meatus following insertion of the urethral plug 10 into the urethra, thereby ensuring a secure placement of the urethral plug 10. An appendage, such as a string 18, is affixed to and extends from the meatal plate 14 and/or body 12 for removal of the urethral plug 10 after insertion. Alternatively, removal may be carried out by the tab 15, a ring 17 (FIG. 1A), or any other removal member adapted to extend from the meatal plate 14 and/or body 12.

Line A—A represents the cross sectional view of the body 12, which will be discussed further with reference to FIGS. 4A and 4B.

Upon insertion of the plug into the urethra, bladder neck and/or bladder, the urethral wall conforms to the plug 10 via an automatic intrinsic reflex of the urethral muscles. The layer of adhesive 16 on the meatal plate 14 serves to anchor the meatal plate 14 at the tissues surrounding the urethral meatus and create a seal therebetween. Retention of the body 12 against the urethral wall is thereby enhanced, such that movement of the plug is arrested and continuous blockage of urine provided. The adhesive layer 16, although shown to be continuous, may be discontinuous, spotty or uneven, depending on the degree of adhesion desired and the condition of the tissues of the user.

FIG. 2 shows an alternative embodiment of the urethral plugs of FIG. 1 and 1A. Shown is a urethral plug 20 having a layer of adhesive 26 on a portion of the body 22. The adhesive layer 26, disposed in such a position, secures the placement of the urethral plug 20 in the urethra by forming a seal with the urethral wall. Upon insertion of the urethral plug 20 into the urethra, bladder neck and/or bladder, the adhesive layer 26 bonds with the urethral wall, such that the wall conforms to the urethral plug 20. This results in a tight seal between the plug 20 and the urethral wall, preventing the urethral plug 20 from moving in any direction. When voiding is desired, the tab 25 of the meatal plate 24, and/or the string 28 affixed to and extending from the urethral plug 20, is grasped and pulled downwardly. The seal between the adhesively-secured portion of the body 22 and the urethral wall is broken, and the urethral plug is removed. Note that, although this figure shows a continuous layer of adhesive 26 on a portion of the body 22, the adhesive layer 26 may be discontinuous, spotty or uneven, depending upon the degree of adhesion desired and the condition of the tissues of the user. Also, the portion of the body bearing the adhesive layer shown in FIG. 2 is exemplary only, and the layer of adhesive may be applied to any suitable portion of the body 22.

To further ensure secure placement of the urethral plug 20, the plug 20 may include an adhesive layer on the meatal plate 24 (not shown) for additional anchoring of the meatal plate 24 against the meatal tissues. The adhesive layer on the meatal plate 24 may be continuous, discontinuous, spotty or uneven. The meatal plate 24 may optionally include a tab 25 extending therefrom.

FIG. 3 shows an alternative embodiment of the urethral plugs of the invention, and for purposes of illustration only, a solid urethral plug 30 is shown. Note, however, that a hollow urethral plug is equally suitable for this embodiment. In this embodiment, the urethral plug 30 has a meatal plate 34 with a layer of adhesive 36 thereon. As provided above, the meatal plate 34 may optionally include a tab 35. The adhesive layer 36 is disposed on the meatal plate 34 so as to anchor and seal the urethral plug 30 against the tissues surrounding the urethral meatus. As shown, the adhesive layer 36 is disposed on the outer circumferential portion of the meatal plate 34, such that a space 37 exists between the adhesive layer 36 and the body 32 of the urethral plug 30. The space 37 is free of adhesive.

The urethral plug 30, with the adhesive layer 36 so disposed, functions to seal the plug at a distance from the urethral meatus. When the user wishes to void, removal is carried out in much the same manner as in the above embodiments. The tab 35 of the meatal plate 34, and/or the string 38, is grasped and pulled downwardly, which breaks the seal formed between the adhesively-secured portion of the meatal plate 34 and the tissues surrounding the urethral meatus. Although FIG. 3 shows a continuous layer of adhesive 36, the adhesive layer may be discontinuous, spotty or uneven. Moreover, this embodiment may optionally include a layer of adhesive on the body 32, or portions thereof, of the urethral plug 30.

Figure 4A:
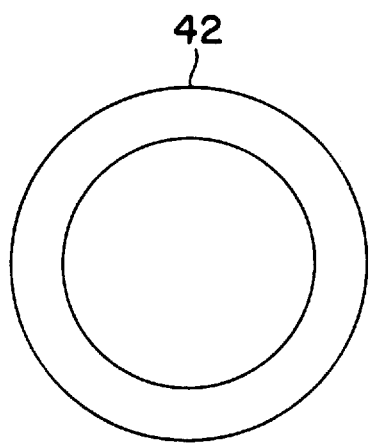
FIG. 4A shows a cross section along line A—A of the body of the urethral plugs in FIGS. 1–2.
Figure 4B:
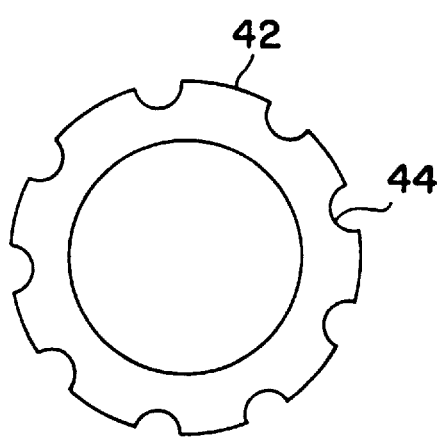
FIG. 4B shows an alternative cross section along line A—A of the body of the urethral plugs in FIGS. 1–2.

FIG. 4A shows a cross sectional view along line A—A of the urethral plugs set forth above in FIGS. 1–2. Body 42 is representative of elements 12 and 22 of the aforementioned urethral plugs, and as shown, is of a substantially constant diameter. FIG. 4B shows an alternative embodiment of the urethral plugs, along line A—A. As shown, the diameter of the body 42 may include curved indentations 44 on the periphery of the body. The indentations 44 provide enhanced surface area by which the urethral plugs may more readily adapt to the urethral wall. Such enhanced sealing ability of the urethral plugs provides a more secure fit for the user.

Figure 5:
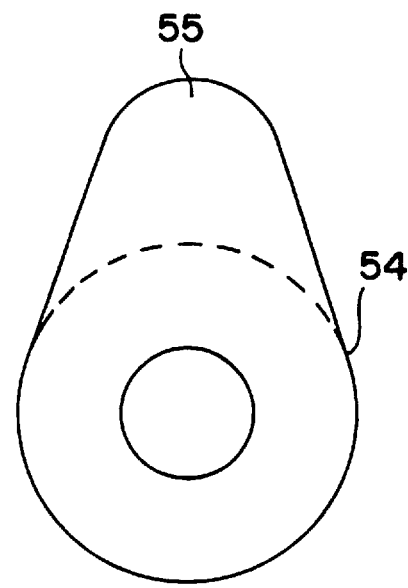
FIG. 5 shows a perspective view of the meatal plate of the urethral plugs in FIGS. 1–2.

FIG. 5 shows a bottom perspective view of a meatal plate 54, which is representative of meatal plates 14 and 24 in the embodiments of FIGS. 1–2. A portion of the meatal plate 54 extends to form a tab 55, which may be grasped by the user for ease of removal.

One skilled in the art will recognize that alternative shapes and configurations can be used for the meatal plate of the urethral plugs of the invention. FIGS. 6A–E illustrate alternative configurations suitable to anchor the plugs to the tissues surrounding the urethral meatus. The shape of the meatal plate will depend on such factors as the user's comfort, gender, the ability of the plate's configuration to be anchored and sealed, and ease of inserting and removing the urethral plug.

Figure 6A:
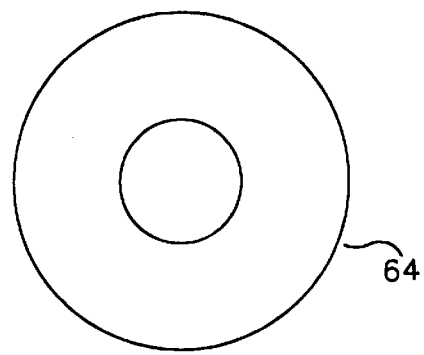
FIGS. 6A–E show alternative configurations of the meatal plate of the urethral plugs of the invention.
Figure 6B:
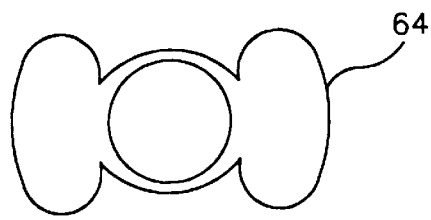
Figure 6C:
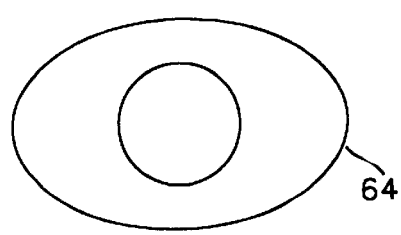
Figure 6D:
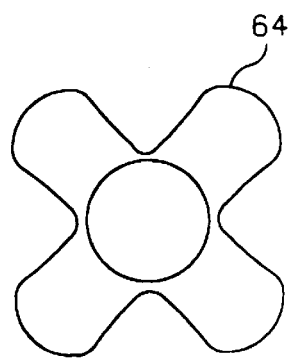
Figure 6E:
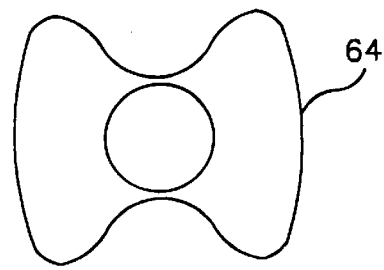

FIG. 6A shows the meatal plate 64 to be circular in shape. The circular meatal plate may be either convex or concave, whichever is more suited for the anatomy of the user. Other meatal plate configurations include, but are not limited to, the dumbbell shape in FIG. 6B, the ovoid shape in FIG. 6C, the star shape in FIG. 6D and the bow tie shape in FIG. 6E.

The configurations of the meatal plate may comprise a three dimensional contour, or may include fold lines to improve the conformability of the meatal plate to the tissues surrounding the urethral meatus and/or the labia.

The method of using the urethral plugs 10, 20 and 30 of the invention is substantially the same. The user inserts the urethral plug into the urethra, bladder neck and/or bladder until the meatal plate abuts and anchors at the urethral meatus. At this point, the layer(s) of adhesive on the meatal plate and/or body of the urethral plug forms a seal with the tissues surrounding the meatus and/or urethra, thereby preventing movement of the urethral plug. The urethral plug is now disposed in the urethra such that it blocks the flow of urine therefrom. When the user wishes to remove the urethral plug, a tug on the tab and/or other appendage, such as a string or ring, breaks the seal formed between the tissues of the user and the adhesive layer(s) on the meatal plate and/or body of the plug. The body of the urethral plug is then withdrawn from the urethra. If desired, a fresh urethral plug may be inserted in the manner set forth above.

While the invention has been particularly shown and described with reference to the aforementioned embodiments, it will be understood by those skilled in the art that various changes in form, composition and detail may be made therein without departing from the spirit and scope of the invention. Thus, any modification to the shape, configuration and/or composition of the elements comprising the invention is within the scope of the invention.

What is claimed is:

1. A remove-to-void urethral plug having enhanced sealing capabilities comprising:
   a non-expandable, hollow body adapted to internally occlude the urethra, the body having a substantially constant cross section, and
   a meatal plate attached to the body, the meatal plate having a layer of adhesive on at least a portion thereof for anchoring the meatal plate at the urethral meatus.

2. The remove-to-void urethral plug according to claim 1 wherein the layer of adhesive is positioned on the meatal plate so as to form a continuous, discontinuous, spotty or uneven layer.

3. The remove-to-void urethral plug according to claim 1 wherein the adhesive is selected from the group consisting of hydrogel adhesives, polyvinylether-based adhesives, hydrocolloid adhesives, acrylic-based adhesives, natural gum adhesives and synthetic rubber adhesives.

4. The remove-to-void urethral plug according to claim 1 wherein the meatal plate has a configuration selected from the group consisting of a circular shape, dumbbell shape, ovoid shape, and bow tie shape.

5. The remove-to-void urethral plug according to claim 1, further comprising an appendage affixed to the meatal plate and extending therefrom.

6. The remove-to-void urethral plug according to claim 1 wherein the body includes curved indentations on the periphery thereof.

7. A remove-to-void urethral plug having enhanced sealing capabilities comprising:
   a non-expandable, hollow body adapted to internally occlude the urethra, the body having a layer of adhesive on at least a portion thereof, and
   a meatal plate for anchoring the body to the urethral meatus,
   whereby the layer of adhesive seals the body against the wall of the urethra such that movement of the plug is arrested.

8. The remove-to-void urethral plug according to claim 7, further comprising a layer of adhesive on at least a portion of the meatal plate.

9. The remove-to-void urethral plug according to claim 8 wherein the layer of adhesive is positioned on the meatal plate so as to form a continuous, discontinuous, spotty or uneven layer.

10. The remove-to-void urethral plug according to claim 7 wherein the adhesive is selected from the group consisting of hydrogel adhesives, polyvinylether-based adhesives, hydrocolloid adhesives, acrylic-based adhesives, natural gum adhesives and synthetic rubber adhesives.

11. The remove-to-void urethral plug according to claim 7 wherein the meatal plate has a configuration selected from the group consisting of a circular shape, dumbbell shape, ovoid shape, and bow tie shape.

12. The remove-to-void urethral plug according to claim 7, further comprising an appendage affixed to the meatal plate and extending therefrom.

13. The remove-to-void urethral plug according to claim 7 wherein the body includes curved indentations on the periphery thereof.

14. A remove-to-void urethral plug having enhanced sealing capabilities comprising:
   a non-expandable body configured to extend into and internally occlude the urethra, the body having a substantially constant cross section, and
   a meatal plate attached to the body, the meatal plate having a layer of adhesive on at least a portion thereof for anchoring the meatal plate at the urethral meatus.

15. The remove-to-void urethral plug according to claim 14 wherein the layer of adhesive is positioned on the meatal plate so as to form a continuous, discontinuous, spotty or uneven layer.

16. The remove-to-void urethral plug according to claim 14 wherein the meatal plate has a configuration selected from the group consisting of a circular shape, dumbbell shape, ovoid shape, and bow tie shape.

17. The remove-to-void urethral plug according to claim 14 wherein the body is hollow.

18. The remove-to-void urethral plug according to claim 14 wherein the body is solid.

19. A remove-to-void urethral plug having enhanced sealing capabilities comprising:
   a non-expandable body adapted to extend into and internally occlude the urethra, the body having a layer of adhesive on at least a portion thereof, and
   a meatal plate for anchoring the body at the urethral meatus,
   whereby the layer of adhesive seals the body against the wall of the urethra such that movement of the plug is arrested.

20. The remove-to-void urethral plug according to claim 19, further comprising a layer of adhesive on at least a portion of the meatal plate.

21. The remove-to-void urethral plug according to claim 20 wherein the layer of adhesive is positioned on the meatal plate so as to form a continuous, discontinuous, spotty or uneven layer.

22. The remove-to-void urethral plug according to claim 19 wherein the meatal plate has a configuration selected from the group consisting of a circular shape, dumbbell shape, ovoid shape, and bow tie shape.

23. The remove-to-void urethral plug according to claim 19 wherein the body is hollow.

24. The remove-to-void urethral plug according to claim 19 wherein the body is solid.

25. A method of using a urethral plug having enhanced sealing capabilities comprising:
   providing a urethral plug having a non-expandable, hollow body substantially constant in cross section and adapted to internally occlude the urethra, the urethral plug further having a meatal plate attached to the body, the meatal plate having a layer of adhesive on at least a portion thereof for anchoring the meatal plate at the urethral meatus.

26. The method of using a urethral plug according to claim 25, further comprising:
   inserting the urethral plug into the urethra, bladder neck or bladder of a user, in a position such that it blocks the flow of urine, and
   adhesively anchoring the meatal plate at the urethral meatus,
   whereby, when the urethral plug is in use, the layer of adhesive on the meatal plate serves to anchor the meatal plate at the meatus, form a seal between the meatal plate and the tissues surrounding the meatus, and enhance a seal of the body to the urethral wall such that movement of the plug is arrested.

27. The method of using a urethral plug according to claim 26, further comprising removing the urethral plug to void.

28. A method of using a urethral plug having enhanced sealing capabilities comprising:

providing a urethral plug having a non-expandable, hollow body adapted to internally occlude the urethra, the body having a layer of adhesive on at least a portion thereof, the urethral plug further having a meatal plate attached to the body for anchoring the meatal plate at the urethral meatus.

29. The method of using a urethral plug according to claim 28, further comprising:

inserting the urethral plug into the urethra, bladder neck or bladder of a user, in a position such that it blocks the flow of urine, and adhesively retaining the body against the wall of the urethra to seal the urethral plug in place without movement or slippage thereof from the inserted position.

30. The method of using a urethral plug according to claim 29, further comprising removing the urethral plug to void.

31. The method of using a urethral plug according to claim 28, further comprising the step of providing the meatal plate with a layer of adhesive on at least a portion thereof so as to seal the meatal plate against the tissues surrounding the urethral meatus.

* * * * *